(12) United States Patent
Buschmann et al.

(10) Patent No.: US 6,332,364 B1
(45) Date of Patent: Dec. 25, 2001

(54) UNIVERSAL MECHANICAL TESTING DEVICE

(75) Inventors: Michael D. Buschmann; Martin Garon, both of Montreal; Matthieu Ouellet, Mont-Royal; Marc Lavertu, Repentigny, all of (CA)

(73) Assignee: Bio Syntech Canada Inc., Laval (CA)

( * ) Notice: Subject to any disclaimer, the term of this patent is extended or adjusted under 35 U.S.C. 154(b) by 0 days.

(21) Appl. No.: 09/553,063

(22) Filed: Apr. 20, 2000

Related U.S. Application Data

(60) Provisional application No. 60/130,520, filed on Apr. 23, 1999.

(51) Int. Cl.[7] .............................. G01N 3/00; G01N 3/48
(52) U.S. Cl. .................................. 73/788; 73/81
(58) Field of Search .................. 73/78, 81, 818, 73/825, 788

(56) References Cited

U.S. PATENT DOCUMENTS

| | | | |
|---|---|---|---|
| 4,074,569 | * | 2/1978 | Sambrook et al. .................. 73/806 |
| 4,299,131 | * | 11/1981 | Seitz et al. ........................... 73/789 |
| 5,005,424 | * | 4/1991 | Markowski ........................... 73/834 |
| 5,301,558 | * | 4/1994 | Livingston et al. ............ 73/862.541 |
| 5,616,857 | * | 4/1997 | Merck, Jr. et al. ..................... 73/82 |
| 5,691,473 | * | 11/1997 | Peleg ..................................... 73/573 |

\* cited by examiner

Primary Examiner—Max Noori
(74) Attorney, Agent, or Firm—Crowell & Moring LLP

(57) ABSTRACT

A universal material testing device which includes a frame; an actuator mounted on the frame for controlling a displacement of a sample to be tested; a load cell movably mounted on the frame and adapted to abut against the sample for detecting a force applied thereon by the actuator, the load cell producing a signal corresponding to the force detected; a signal conditioning unit for reducing input noise and for processing of the signal and executing specific tests by coordination of displacement control and load signals received for processing from the load cell; and a detachable chamber with humidifying media for humidification of the sample environment confined within the chamber and separated frm the sample so as to avoid potential damaging effects of humidity on the sample or on the device. The device is useful for determining certain material properties of a sample.

22 Claims, 11 Drawing Sheets

(ALL THE DISPLACEMENTS ARE OF 0.025 μm)

UNIVERSAL MECHANICAL TESTING DEVICE

CROSS REFERENCE TO RELATED APPLICATION

This application claims priority from co-pending U.S. provisional patent application No. 60/130,520 filed Apr. 23, 1999.

BACKGROUND OF THE INVENTION (a) Field of the Invention

The invention relates to a universal testing device for determining certain material properties of a sample.

(b) Description of Prior Art

Material testing refers to the evaluation of mechanical properties of solid materials by simultaneously measuring material deformation (displacement) and stress (force). The technical area is mature and highly developed with respect to industrial sized objects with dimension of centimeters or larger. When specimen dimensions encroach upon millimeters instrumentation and methods are less well developed, due to precision and control difficulties. When materials are soft in addition to small, technical difficulties also arise in eliminating noise from force signals.

Material testing systems are often developed with precise goals in mind. Thus some systems provide mechanical configurations appropriate for adhesion and tack tests (U.S. Pat. No. 5,438,863) for extrusion of thermoplastics in rheological testing (U.S. Pat. No. 4,680,958) and others for hardness and bonding tests of pharmaceuticals (U.S. Pat. Nos. 4,780,465, and 5,140,861). Common technical hurdles in these specific applications are precise control of displacement and low noise acquisition of force and displacement. These problems are overcome to varying degrees but generally insufficiently so in modern instruments. Also in spite of the underlying commonality in all material testing which is control and acquisition of force and displacement, instruments are often conceived and designed for the application of a limited number of tests where, for example, only one type of displacement is applied to obtain a certain force response upon which a particular analysis yields one characteristic material parameter. The limited flexibility of such systems is evident since proper mechanical and electrical design combined with algorithmic computer control of tests can in principle provide a universal system capable of executing the full range of material tests on small samples, as has been achieved for industrial sized objects. For example common measures of adhesion, tack, hardness, strength, modulus, viscoelasticity, plasticity etc. can all be obtained by parametric control of a limited number of fundamental tests such as ramp, stress relaxation, dynamic sinusoidal and creep tests.

In the biomedical domain of material testing, a particular need for testing samples in aqueous solutions under controlled environments of atmospheric gas composition and humidity arises. In the absence of material testing needs, these environments are generally provided by cell or tissue culture incubators. In the past, the need to perform material tests under these controlled environments has been addressed by developing testing chambers specific to the material testing apparatus to provide environmental control, since the material testing device is usually much too large to be placed in an incubator.

It would thus be highly desirable to be provided with a material testing instrument that would allow testing of these small specimens and that could be designed so as to fit inside a standard tissue culture incubator, thus adding to the universality of the device by including biomedical applications in their most standard format.

SUMMARY OF THE INVENTION

One aim of the present invention is to provide a precise and controlled material testing device for testing small specimens.

Another aim of the present invention is to provide a material testing device that could be designed so as to fit inside a standard tissue culture incubator, thus adding to the universality of the device by including biomedical applications in their most standard format.

Another aim of the present invention is to provide a material testing device for performing stress relaxation test, ramp-release test, Creep test, dynamic sinusoid measurements, long sinusoids, using an actuator for moving a sample at a constant speed, in which the actuator is so controlled as to mimic sinusoidal or other displacement, when needed.

Another aim of the present invention is to provide a material testing device for testing for unconfined or confined compression test, indentation test, tension test, and bending test.

In accordance with the present invention, there is provided a universal material testing device comprising:

a) a frame;

b) an actuator mounted on the frame for controlling a displacement of a sample to be tested;

c) a load cell movably mounted on the frame and adapted to abut against the sample for detecting a force applied thereon by the actuator, the load cell producing a signal corresponding to the force detected; and d) a signal conditioning unit for reducing input noise and for processing of the signal and executing specific tests by coordination of displacement control and load signals received for processing from the load cell.

In one embodiment of the invention, the signal conditioning unit is a force sensing amplifier device.

In a variant on the invention, the frame may further comprises a crossbar for receiving the load cell, the crossbar having a minimal mass and minimal vertical deflection for not increasing device compliance while still exerting minimal resting force on an attached load cell, to avoid damaging of the latter.

The crossbar is preferably slidably adapted onto the frame for sliding in a vertical direction, the crossbar being removably fixed at a given height on the frame by manual retention means. The retention means may be for example butterfly bolts.

The device may also further comprising means for attaining fine vertical alignment with a sample fixed to the actuator. The means for attaining fine vertical alignment may comprise for example an enlarged bore hole through the crossbar, two rigid washers on each side of the bore hole and a bolt traversing the hole attached to the load cell, whereby in use fine vertical alignment with the sample is achieved visually by sliding the bolt and washers across the crossbar using the tolerance provided by the enlarged bore diameter.

The device may further comprise a test chamber for unconfined compression of a sample. The test chamber is mounted on the device for allowing the load cell to access within.

The device may alternatively further comprise a test chamber for confined compression of a sample, the test chamber being mounted on the actuator and provided with a bore adapted in size to receive in a fit-tight manner the load cell for measuring confined compression on a sample placed within the bore.

The load cell may be provided with an indentor for testing indentation of a sample.

The device may also comprise a test chamber for tension testing of a sample attached therein, the load cell being provided with grips for retaining and pulling on one end of the sample.

The device may also further comprise a test chamber attached to and suspended from the load cell, the load cell being connected to the actuator supported by the crossbar, wherein the crossbar is mounted on the frame for vertical movement, the actuator, the load cell and the chamber being aligned in one axis.

The device may also comprise a test chamber having a floor and being adapted for bending tests, the test chamber being provided with supports for supporting a sample above the floor of the chamber.

Still in accordance with the present invention, the device may also comprise a test chamber provided with microelectrodes incorporated into the test chamber to detect electrical events caused by compression induced streaming potentials within the sample during testing.

The device may further comprise a detachable chamber designed to be autoclave sterilized and to accept sterile specimens within an aseptic environment for testing in a sterile environment. The detachable chamber may further comprise a humidifying media for humidification of the sample environment confined within the chamber and separated from the sample so as to avoid potential damaging effects of humidity on the sample or on the device.

The device may further comprise a programmable digitizing amplifier situated in the vicinity of the load sensing unit to i) minimize noise in the load signal by providing a digital signal representing the load with a precision of 1 part in 20,000 ii) accommodate interchangeable load cells with specific energizing and gain parameters, and iii) provide a second digital output indicating a user defined excess load (overload) condition on the load cell. The digital signal indicating excess load may preferably be directly coupled to the actuator controller to automatically execute a motor stop command in response to excess load.

The actuator preferably provides a precision of 1–1000 nm with a range of at least 0.25–5 million times that value and executes a constant velocity motion, the actuator being controlled with a computer program to execute stress relaxation, ramp-release, dynamic sinusoidal and creep tests, the stress relaxation refers to the application of a constant velocity displacement followed by a hold phase while measuring force, the ramp-release refers to the application of a constant velocity displacement followed by the reverse of that displacement to obtain the initial position, the dynamic sinusoids refers to the application of a displacement in the form of a sinusoidal wave of high precision and low total harmonic distortion, and the creep refers to the application of a constant force by feedback control of the actuator position.

During a sinusoidal test, a sinusoidal displacement of the actuator is preferably achieved using a computer algorithm concatenating a sequence of constant velocity steps to achieve an optimal precision and minimal distortion of the sinusoidal displacement, given the amplitude and frequency of the sinusoidal displacement, the algorithm finds a sequence of constant velocity steps which best approximate the sine wave given the performance characteristics of the actuator (including step size and velocity range).

During a creep test, a feedback control of the actuator is preferably executed to maintain a constant sensed force on the load cell, a computer algorithm is used where an updated position is calculated to maintain a constant sensed force, based on the force and position history and performance characteristics of the actuator, step size and velocity range of the actuator.

The signal conditioning and treatment include an interpolation algorithm to temporally align the position and force signals given known performance characteristics of a signal acquisition system including the delay time between acquisition of load and position.

An initial contact of the sample and the load cell is preferably found using an automated computer controlled procedure where an algorithm applies a calculated displacement at a calculated velocity until a given value of contact force is detected by the cell load.

Further in accordance with the present invention, there is provided a universal material testing device comprising:

a) a frame;

b) an actuator mounted on the frame for displacement of a sample to be tested;

c) a force sensing device mounted on the frame, for detecting a force applied on the sample by the actuator, the force sensing device emitting a signal in response to detection of a force;

d) a signal conditioning unit for receiving the signal from the force sensing device and reducing input noise from the signal;

e) an actuator controller connected to the actuator for controlling the actuator; and f) means for processing of the signal and for executing specific tests by coordination of displacement control and load signals.

BRIEF DESCRIPTION OF THE DRAWINGS

Having thus generally described the nature of the invention, reference will now be made to the accompanying drawings, showing by way of illustration a preferred embodiment thereof, and wherein.

DETAILED DESCRIPTION OF THE INVENTION

Figure 1B:
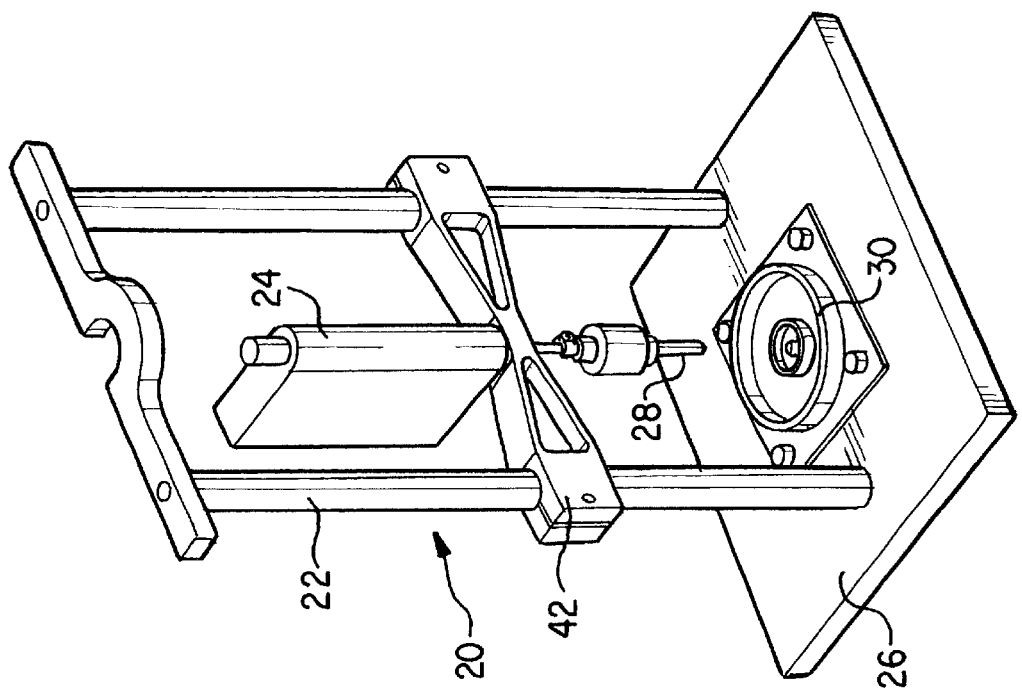
FIG. 1B is a perspective view of the second configuration of a material testing device in accordance with a preferred embodiment of the invention.
Figure 1A:
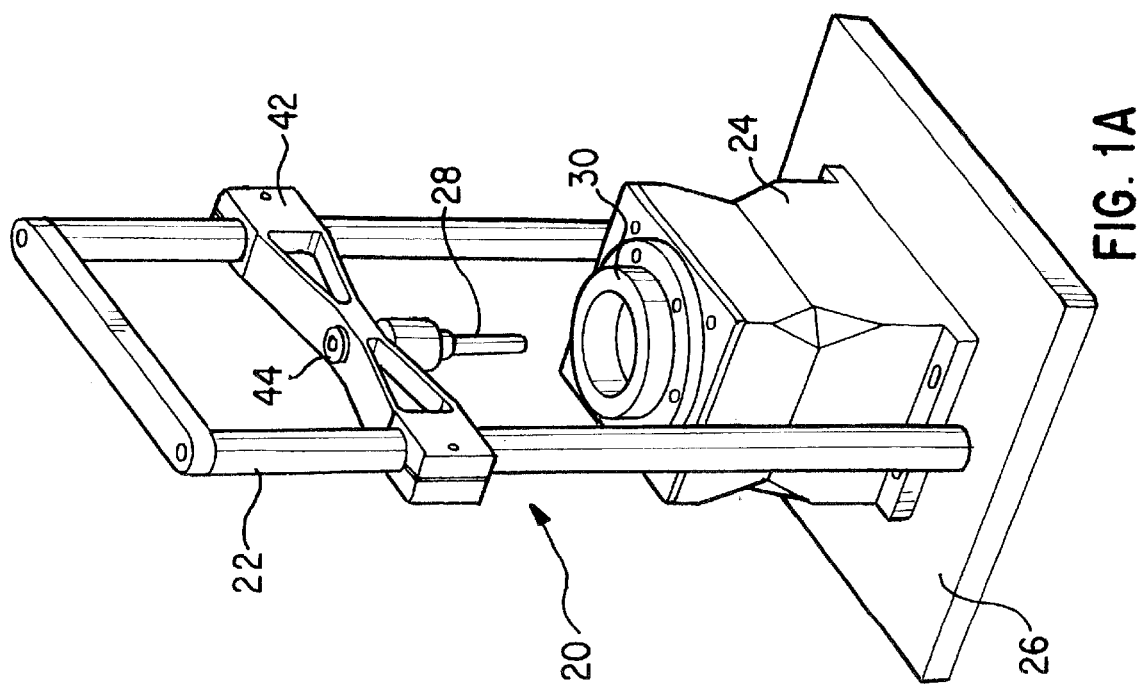
FIG. 1A is a perspective view of the first configuration of a material testing device in accordance with a preferred embodiment of the invention.

FIGS. 1A and 1B illustrate a device 20 in accordance with the present invention, which comprises a frame 22, an actuator 24, a universal platform 26, a load sensing unit 28 (also called load cell), a signal conditioning unit and a computerized algorithmic control for execution and analysis of tests. Precision of 1 part in 20,000 for load measurement (5 mg) and 1 part in 1,000,000 for position control (25 nm) is preferably used in the execution of stress relaxation, ramp, dynamic sinusoidal and creep tests.

The universal platform 26 on both configurations accepts a test chamber 30 for compression tests (FIGS. 2 and 3), indentation tests (FIG. 4), bending tests (FIG. 6), and tension tests. The tension test configuration illustrated on FIG. 5A may be adapted to fit on the device illustrated on FIG. 1A and the tension test configuration illustrated on FIG. 5B may be adapted to fit on the device illustrated on FIG. 1B. The frame 22 including actuator 24 and load sensing unit 28 is designed to fit inside a tissue culture incubator for testing in controlled environments using, if needed, an autoclave sterilized testing chamber. Attention is paid to ease of use and universality of all features and functions to provide a means for material testing of tissues, pharmaceuticals, adhesives, polymers and gels.

Figure 5A:
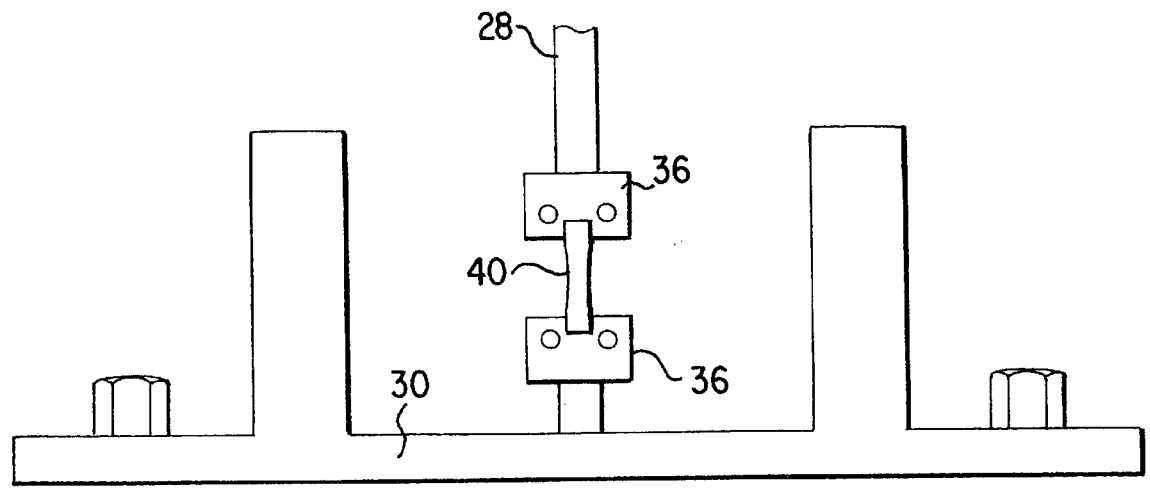
FIG. 5A is a side elevation view of another testing configuration of the material testing device of the present invention used for tension test.
Figure 5B:
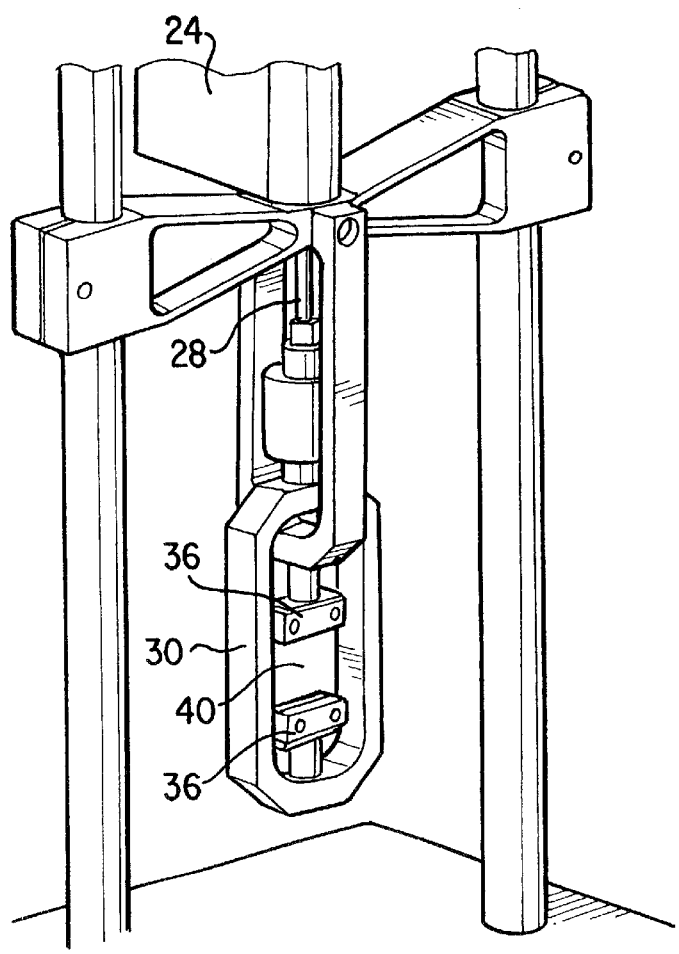
FIG. 5B is a side elevation view of another testing configuration of the material testing device of the present invention used for tension test.

A tension test is perform in FIG. 5B in a way that takes advantage of a compressive or extension movement of the actuator 24 and to avoids the induction of any bending moments (a common axis is present). A major practical advantage of this design is the open space below the grips 36 and sample 40 allowing for the introduction of any bathing chamber or other controlled environment device.

In the device of the present invention, the crossbar 42 is designed such that it has a minimal mass and minimal vertical deflection, for not increasing system compliance (negligible deflection) while still exerting minimal resting force on an attached load cell 28 in order to avoid damaging of the latter. A preferred embodiment of the crossbar 42 is illustrated in FIG. 1A The means for fixing the vertically sliding crossbar 42 at a particular height could be any means suitable for the functions of holding the crossbar, such as butterfly bolts tightened and loosened by an operator, thus utilizing a variation of manual fasteners appropriate for this purpose.

In a particular embodiment of the invention, for attaining vertical alignment with a specimen fixed to the actuator, an enlarged bore hole is provided through the crossbar, two rigid washers 44 on each side of the bore hole and a bolt traversing the hole attaching to the load cell 28. Alignment is achieved visually by sliding the bolt/washers system across the surface of the crossbar using the tolerance provided by the enlarged bore diameter.

The overall system dimensions and materials are preferably compatible with placement in a standard cell or tissue culture incubator having for example interior dimension of 2 feet wide by 2 feet deep by 3 feet high). Atmospheric conditions in an incubator are typically 37° C., 5% $CO_2$ and 95% relative humidity.

Figure 2:
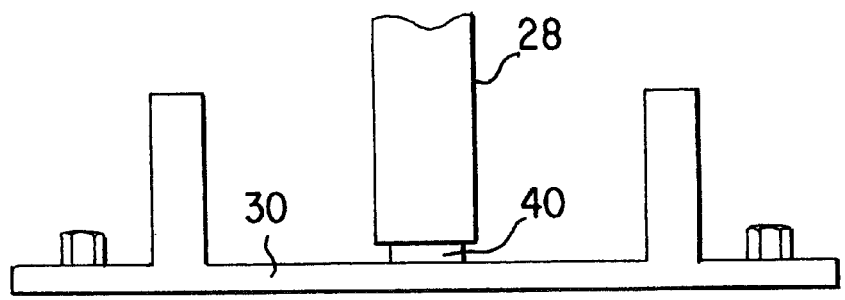
FIG. 2 is a side elevation view of a testing configuration of the material testing device of the present invention used for testing unconfined compression.

Many test chambers may alternately be attached to the device of the present invention so as to provide a single device for carrying out a multitude of tests. Accordingly, FIG. 2 illustrates a test chamber for unconfined compression of a sample attached to the actuator and force sensing unit for use with the device of the present invention.

Figure 3:
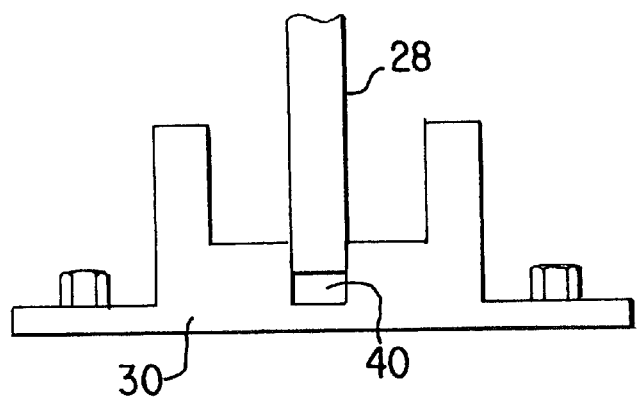
FIG. 3 is a side elevation view of another testing configuration of the material testing device of the present invention used for testing confined compression.

FIG. 3 illustrates a test chamber 30 for confined compression of a sample 40 compressed between the actuator 24 and load cell 28 (force sensing unit) also for use with the device of the present invention.

Figure 4:
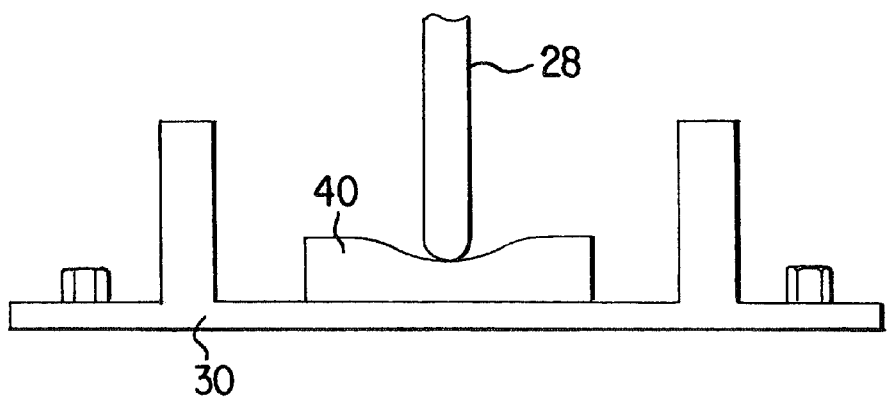
FIG. 4 is a side elevation view of another testing configuration of the material testing device of the present invention used for testing indentation.

FIG. 4 illustrates another test chamber 30 for indentation of a sample 40 compressed between the actuator 24 and load cell 28 or force sensing unit.

FIGS. 5A and 5B illustrates another test chamber 30 for tension testing of a sample 40 attached to the actuator 24 and load cell 28.

Figure 6:
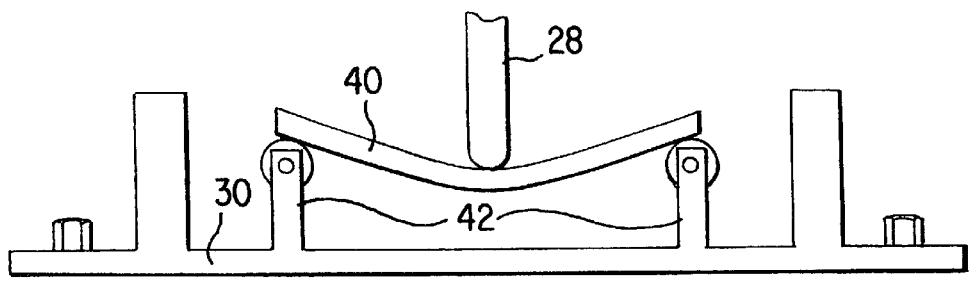
FIG. 6 is a side elevation view of another testing configuration of the material testing device of the present invention used for bending test.

FIG. 6 illustrates a further test chamber 30 for a bending test of a sample 40 between the load cell 28 moved by the activator and two adjustable supports 42.

Figure 7:
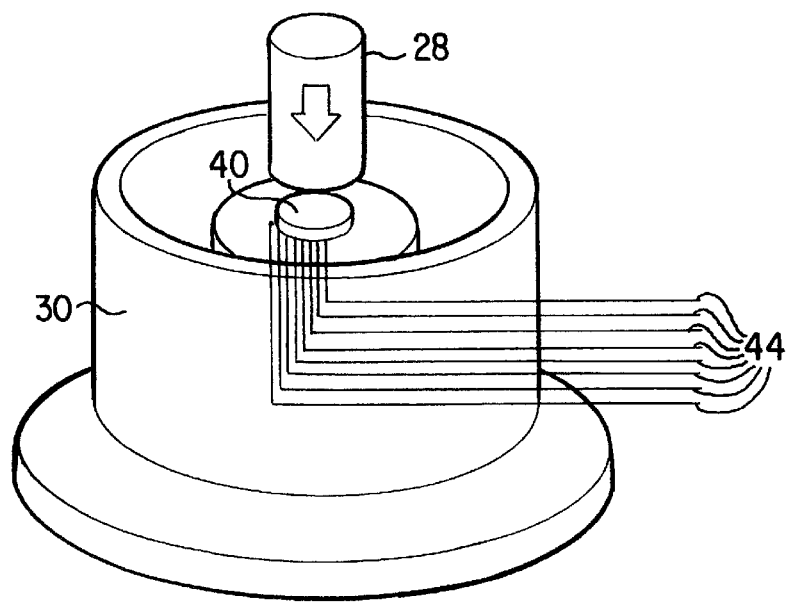
FIG. 7 is a side elevation view of another testing configuration of the material testing device of the present invention used for measuring variation of electric potential.

The system of the present invention may further comprise microelectrodes 44 incorporated into the testing chamber 30 to detect electrical events occurring during testing. An example of such microelectrodes is the system of electrodes incorporated into an unconfined compression chamber to measure compression induced streaming potentials (FIG. 7).

Figure 8:
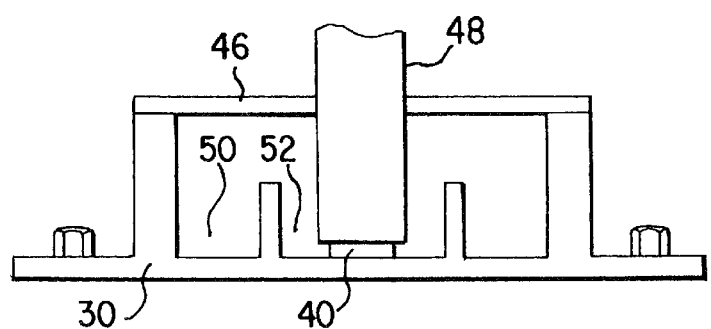
FIG. 8 is a side elevation view of a humidifying testing chamber of the material testing device of the present invention.

In a particular embodiment of the invention illustrated in FIG. 8, the chamber 30 of the device 20 of the present invention is designed to be autoclave sterilized and to accept sterile specimens within an aseptic environment before transfer to a non-aseptic environment (tissue culture incubator) for testing in a controlled environment, while maintaining sterility. Accordingly, the chamber 30 may be provided with a cover 46 to maintain sterile condition. A hole is provided in the cover 46 with a tolerance of 0.0005 for insertion of a rod 48 mounted to the load cell.

Testing chambers may also be designed so as confine humidification of the sample environment to the interior of the chamber via the inclusion of a humidifying section 50 containing an aqueous solution separated from the bathing media 52 of the sample 40. Such chambers avoid potential damaging effects of humidity on the electronic components of the actuator or other parts of the system present inside the incubator (FIG. 8.).

A programmable digitizing amplifier situated in the vicinity of the load sensing unit is preferably used to i) minimize noise in the load signal by providing a digital signal representing the load with a precision of 1 part in 20,000 ii) accommodate interchangeable load cells with specific energizing and gain parameters, and iii) provide a second digital output indicating a user defined excess load (overload) condition on the load cell.

The digital signal indicating excess load is preferably coupled directly to the actuator controller to automatically execute a motor stop command in response to excess load.

The actuator (providing a precision of 1–1000 nm with a range of at least 0.25–5 million times that value) executing constant velocity motion is controlled with a computer program to execute stress relaxation, ramp-release, dynamic sinusoidal and creep tests.

Stress relaxation refers to the application of a constant velocity displacement followed by a hold phase while measuring force.

The stress relaxation measurement routine allows to apply sequences of ramp-hold displacements, i.e. stress relaxation tests for a viscoelastic material. A sequence of ramp-hold displacements is specified by deciding on the number of ramps and the amplitude and velocity of each ramp. There are two ways of determining the end of each relaxation profile before applying the next ramp. The first is to simply specify the time of acquisition of each profile. The second is to measure the slope of load vs. time and end the profile when this slope is less than a criterion that you specify. With the latter technique a uniform estimation of equilibrium is made throughout the acquisition. The decision to end the relaxation profile using the slope calculation is affected not only by the slope criterion but by the "Sample Time" and the "Time for Measurement of the Slope"—small "Sample Time" and large "Time for Measurement of the Slope" allow the use of very strict criterion for equilibrium since the effect of noise on the slope calculation is minimized.

Ramp-release refers to the application of a constant velocity displacement followed by the reverse of that displacement to obtain the initial position.

The Ramp-Release routine executes a sequence of displacements (tension or compression) followed by a release each at the same constant velocity. This routine and the Long Sinusoid routine are particularly useful for mechanically stimulating specimens, especially in controlled environments such as cell or tissue culture incubators. It is also useful for studying fatigue and related processes during prolonged loading periods. In addition to defining the amplitude and velocity of the displacement, two time parameters are defined—the time spent between the displacement and release ("Rest Time at Peak") and the time following the release before the next displacement is executed ("Rest Time Between Cycles"). A sequence of identical displacements and releases is then executed to completion. Since loading times can be extended and total data volume massive, there is an option of saving less than the entire data set by setting "Save Every? Cycles" to a number other than 1 and by "Reducing Acquisition Time After Each Cycle".

Creep test refers to the application of a constant force by feedback control of the actuator position.

The only difference between the creep and the stress relaxation routine is the following. The stress Relaxation holds the position constant at the end of the ramp displacement, whereas the creep holds the load constant at the end of the ramp displacement.

"Dynamic sinusoids" refers to the application of a displacement in the form of a sinusoidal wave of high precision and low total harmonic distortion.

The dynamic sinusoids measurement routine allows execution of sinusoidal displacements from $10^{-5}$ to 1 Hz with amplitudes in the range 0.5 μm to 10 mm. For the larger amplitudes care must be taken that the extreme of the sinusoids are within the range of the actuator (26 mm). The routine executes a sequence of sinusoidal displacements determined by the arrays "Amplitudes", "Frequencies" and "Cycles". The execution order is the first amplitude with all the frequencies followed by the second amplitude with all of the frequencies etc. The "Number of Amplitudes" and the "Number of Frequencies" to be executed from each array are controlled by integer values. Each "Frequency" has a number of "Cycles" to be executed and a number of "Cycles to wait before FFT". The latter refers to the number of cycles during which the transient response decays to negligible values, and after which Fourier analysis is applied to obtain amplitudes and phases of fundamentals and harmonics of the position and load. It is also important to properly specify the "Time Between Sinusoids"; equilibrium should be attained before applying the next sinusoid. The execution time can be estimated before starting.

The Long Sinusoid routine is used when sinusoidal displacements of a given frequency and amplitude is desired over an extended period of time, such as when mechanically stimulating specimens, especially in controlled environments such as cell or tissue culture incubators. It is also useful for studying fatigue and related processes during prolonged loading periods. The amplitude, frequency and duration of loading are defined.

Figure 9A:
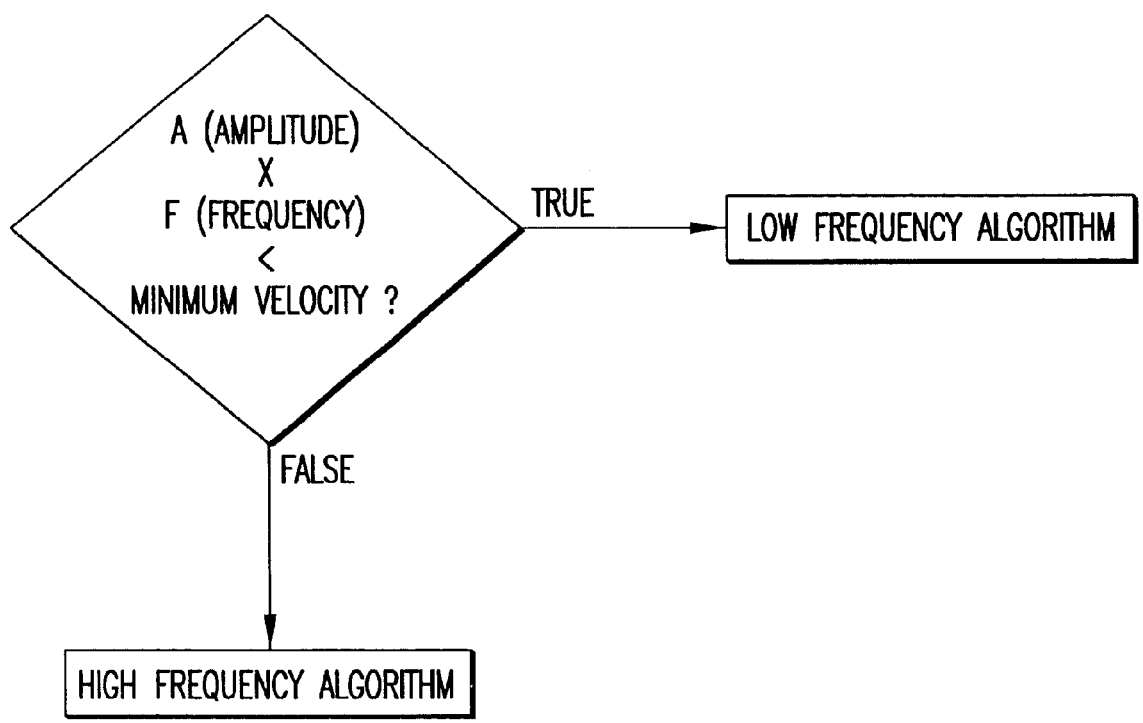
FIGS. 9A to 9C represent flow chart of a sinusoidal algorithm developed for moving the actuator of the material testing device of the present invention.
Figure 9B:
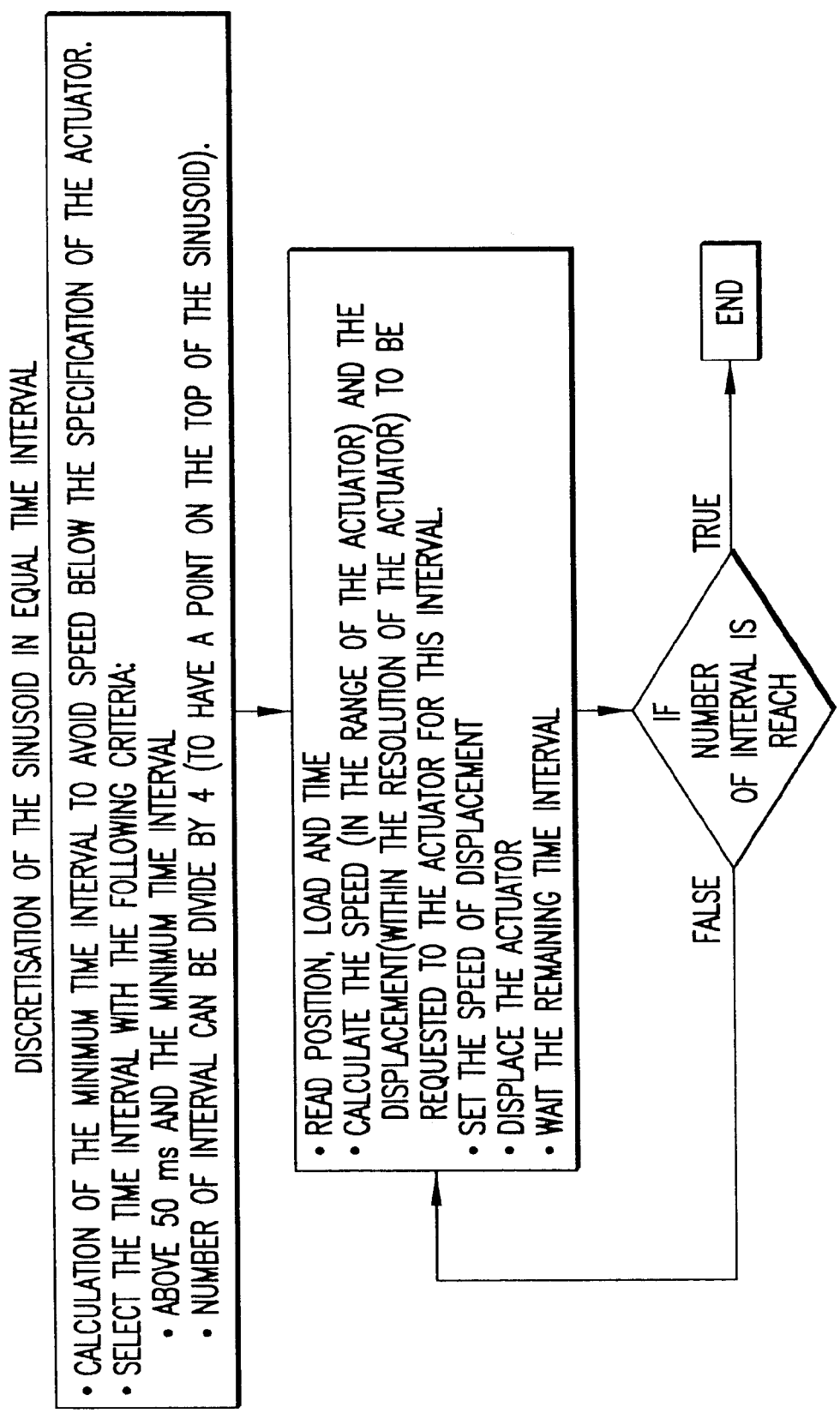
Figure 9C:
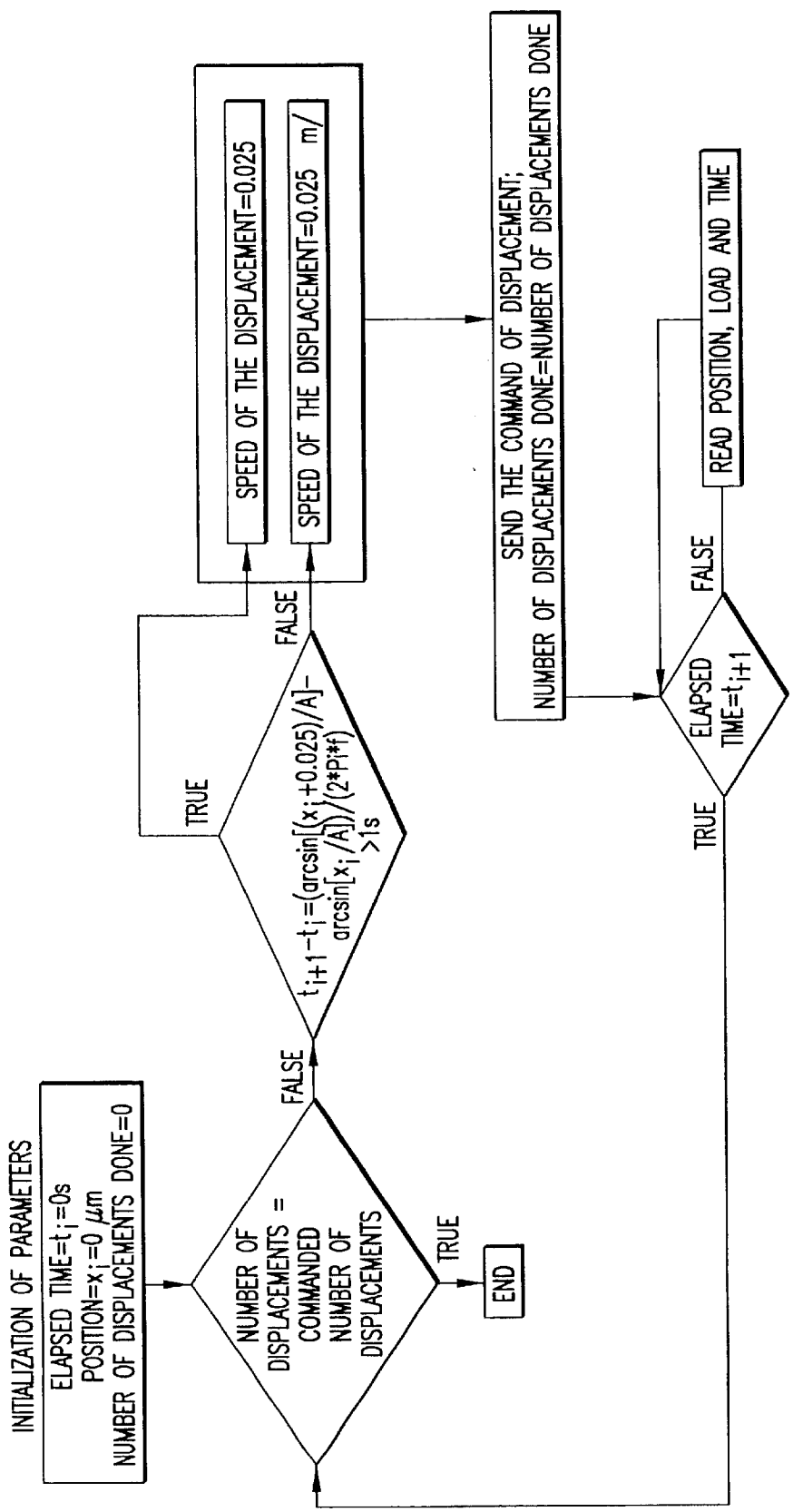

The sinusoidal displacement of the actuator is achieved using a computer algorithm concatenating a sequence of constant velocity steps to achieve an optimal precision and minimal distortion of the sinusoidal displacement. Given the amplitude and frequency of the sinusoidal displacement, the algorithm finds a sequence of constant velocity steps which best approximate the sine wave given the performance characteristics of the actuator (including step size and velocity range) (FIGS. 9A to 9C).

Figure 10:
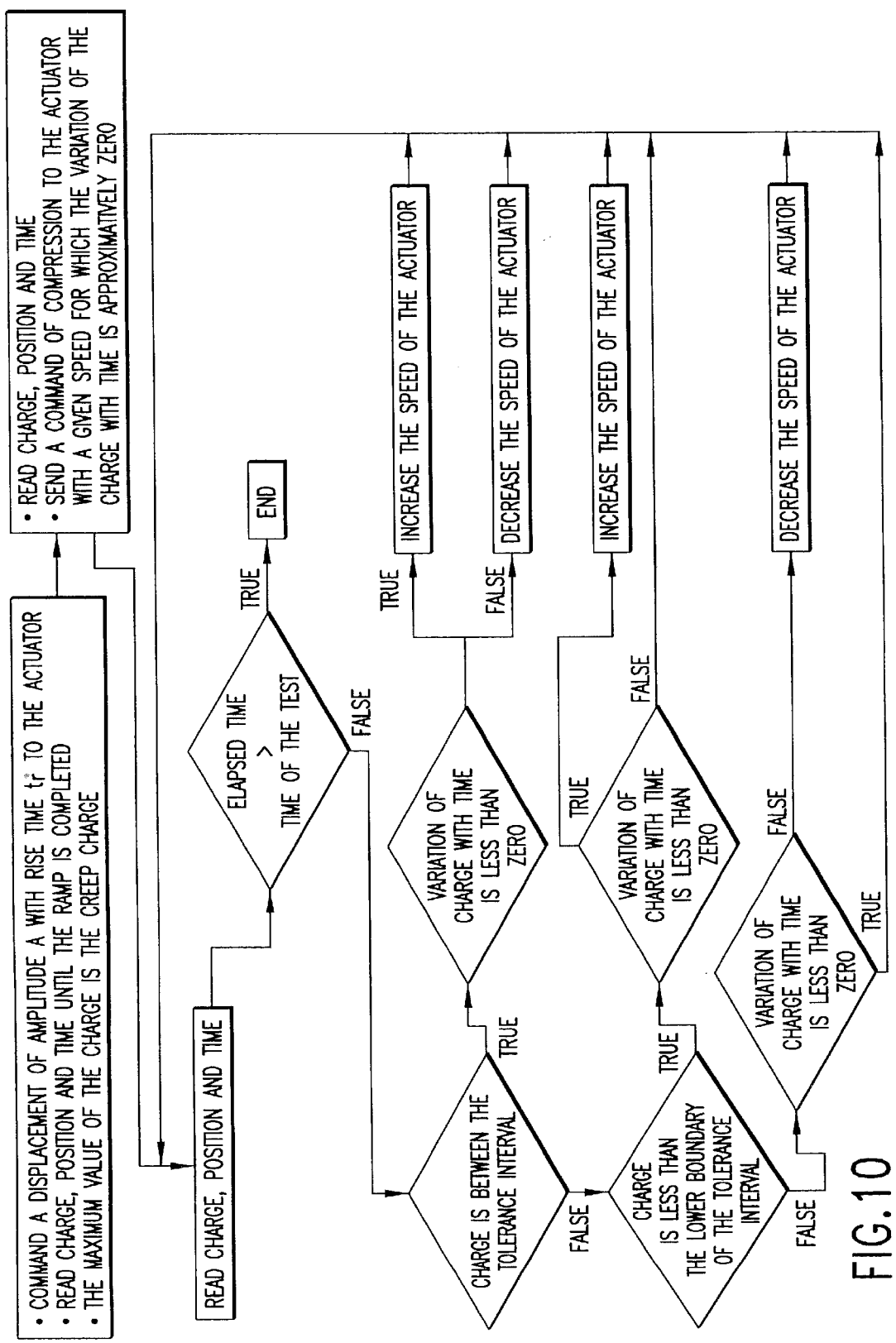
FIG. 10 represents a flow chart developed for performing a creep test with the material testing device of the present invention.

The creep test is executed by feedback control of the actuator to maintain a constant sensed force on the load cell. Another computer algorithm is used where an updated position is calculated to maintain a constant sensed force, based on the force and position history and the performance characteristics of the actuator (including step size and velocity range) (FIG. 10).

Figure 11:
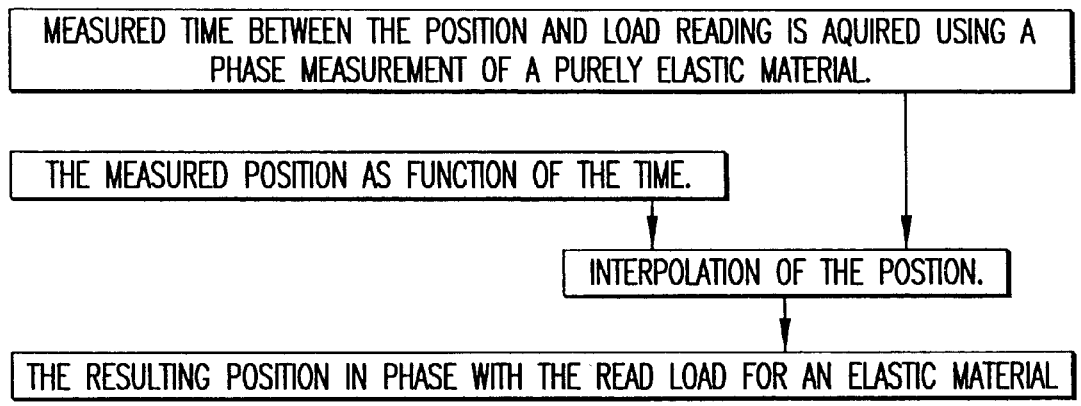
FIG. 11 represents a flow chart developed for correcting and synchronizing position and force measurements obtained with the material testing device of the present invention.
Figure 12:
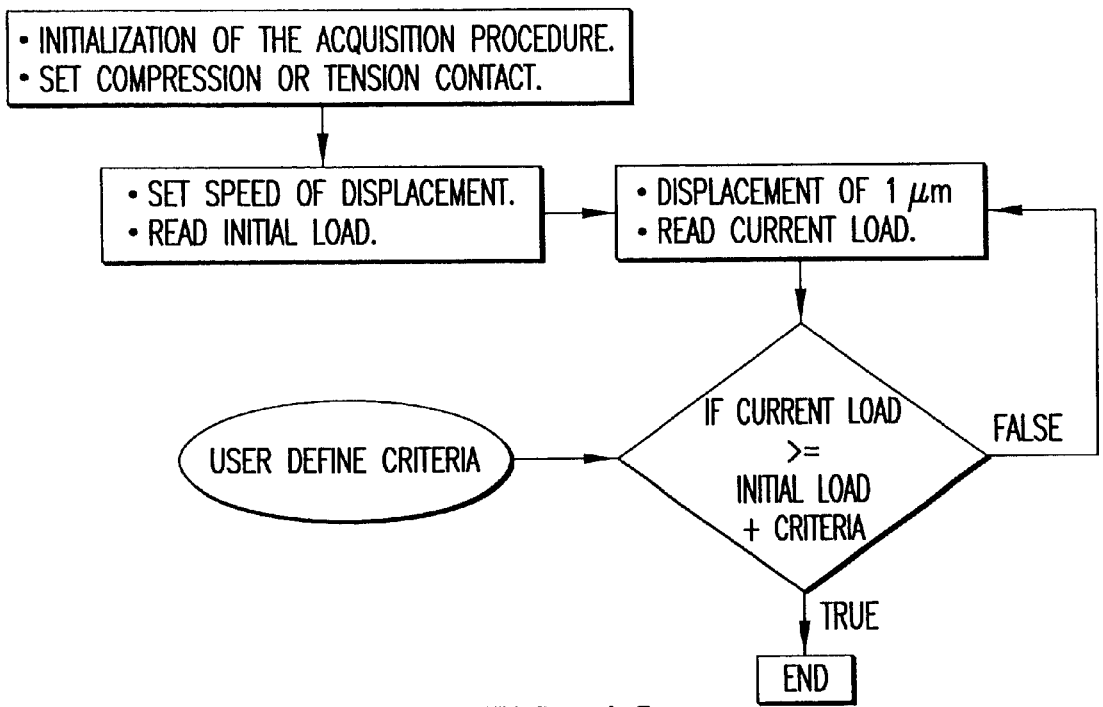
FIG. 12 represents a flow chart developed for setting up the material testing device of the present invention.

The system of the present invention may also comprises an interpolation algorithm to temporally align the position and force signals given known performance characteristics of the signal acquisition system including the delay time between acquisition of load and position (FIG. 11), for signal conditioning and treatment.

Where initial contact of the sample and load cell is found using an automated computer controlled procedure, an algorithm applies a constant displacement at a constant velocity until a given value of contact force is detected by the force sensing element (FIG. 12).

Figure 13A:
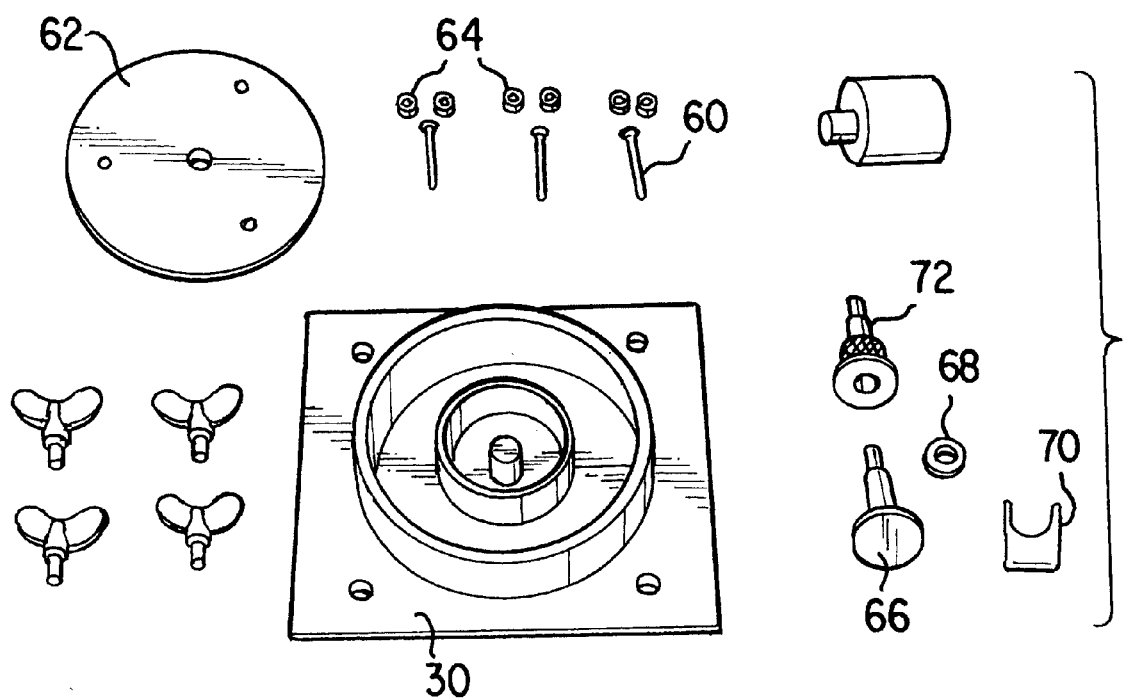
FIGS. 13A to 13C illustrate the elements of a humidifying chamber, and its assembly.
Figure 13B:
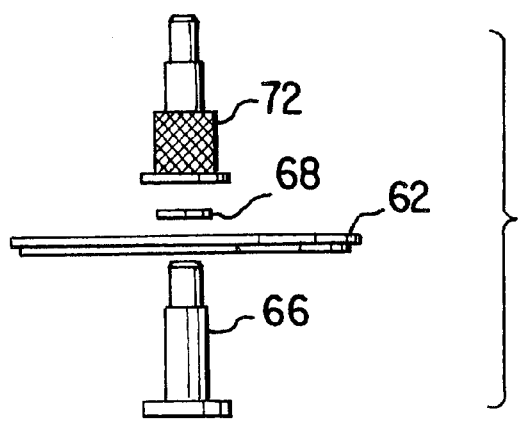
Figure 13C:
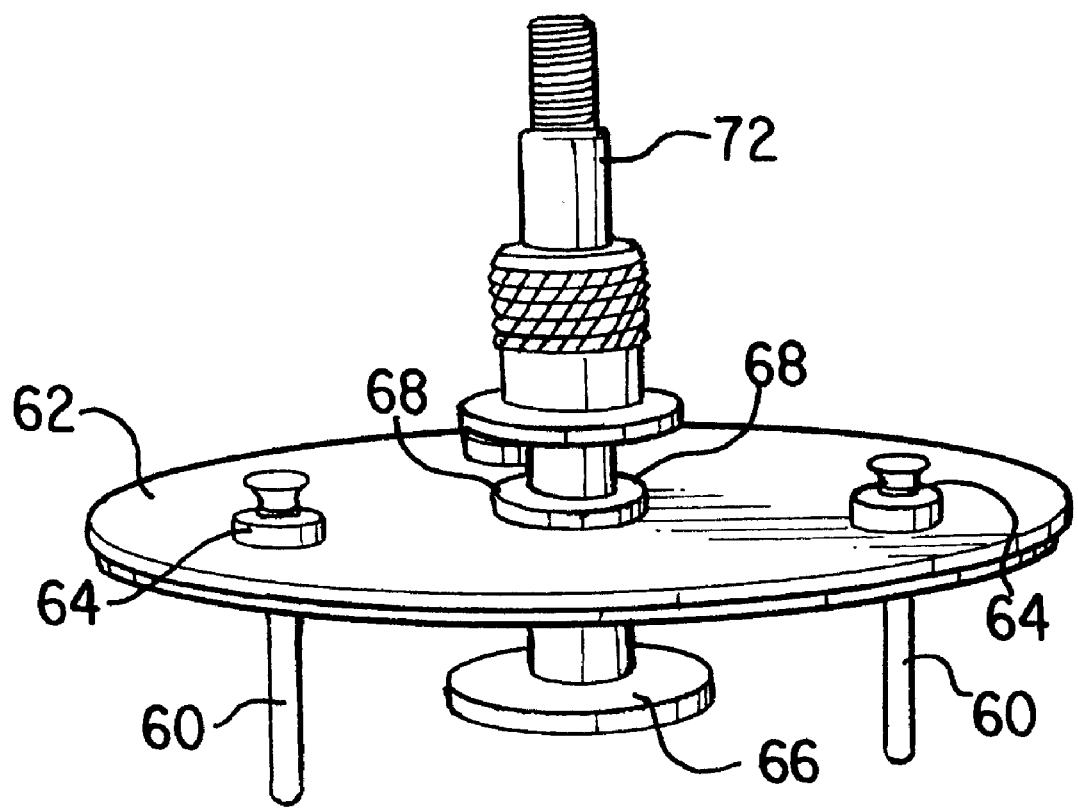

FIGS. 13A to 13C illustrate the elements of a humidifying chamber 30, and its assembly. Stands 60 are mounted on the cover 62 with a double lock screw 64 system. For mounting the rod through the cover, a lower rod 66 is first inserted through the cover 62. A washer 68 and a spacer 70 are then inserted in the lower rod 66 emerging from the other side of the cover 62. An upper rod 72, at one end thereof, is then screwed to the lower rod 66. The other end of the upper rod 72 is to be screwed to the cell load. For doing so, the upper rod 72 is centered with the load cell, and the upper rod is screwed thereto. Once the upper rod is screwed to the load cell, the spacer is then removed.

In use under sterile conditions, a sample is placed in the middle of the center ring with an appropriate testing media. The autoclaved outer ring is then filled with water and the chamber is closed with the cover.

The actuator and actuator controller can be any standard one but there are four important parameters to consider in the choosing it: the minimal and maximal velocities, the spatial resolution of the actuator, and the response time of the controller. All of these parameters will be important in the sinusoidal and creep algorithms.

The load cell amplifier can be any standard load cell amplifier but there are two important parameters to consider in the choosing it. These are the resolution of the amplifier and the possibility to be user programmable to allow it to be used with different load cells.

Four important parameters are to be considered in the choosing of a load cell. These are a minimal deformation of the load cell, a minimal non-linearity, a minimal temperature effect and the maximal mV output.

The crossbar illustrated in FIGS. 1A and 1B is designed with three major restrictions:

1) A deformation, at its center, of less than 1 $\mu$m for an applied force of 100 Newton so that this deformation is negligible in comparison of the deformation of the sample.
2) A mass of less than 1 kg to allow a user to deposit the crossbar on the load cell, for the configuration show in FIG. 1A, as a reference for the position of the actuator. The mass of 1 kg is chosen so as to be below the capacity of the load cell and thus to avoid an over load for a 1 kg load cell.
3) The crossbar can easily be moved to allow changes in the measurement configuration. (i.e. Indentation, Electrodes, humidifying chamber, etc . . . ).

The materials used for the crossbar, the frame and all the chambers except the chamber for the electrode are 316, 316L and 304 Stainless Steel. For the electrode, a Delrin™ layer is added to have a non-conductive bath. Delrin is a commercial designation for a polyoxymethylene (POM) plastic.

This description demonstrates the best way to use our system and obtain best results in the case of a compression test.

First, calibrate the load cell with the incorporated sub-routine. Deposit the crossbar with the load cell and the testing rod on the testing chamber and set this position of the actuator as the reference. Move down the actuator and put a sample in the testing chamber. Move back up the actuator with the "find contact" routine as illustrated in FIG. 12. From the actual position of the actuator the thickness of the sample can be deduced. From this point any available test can be performed, like a creep test, a stress relaxation test or a sinusoid test.

For calibration, the load on the "loaded" load cell is read. The load on the "unloaded" load cell is also read. Finally, the calibration factor is calculated with the following formula: Calibration factor=heavy load weight/(Read "loaded"-Read "unloaded").

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

What is claimed is:

1. A universal material testing device comprising:
   a) a frame;
   b) an actuator mounted on said frame for controlling a displacement of a sample to be tested;
   c) a load cell movably mounted on said frame and adapted to abut against said sample for detecting a force applied thereon by said actuator, said load cell producing a signal corresponding to the force detected;
   d) a signal conditioning unit for reducing input noise and for processing of said signal and executing specific tests by coordination of displacement control and load signals received for processing from the load cell; and
   e) a detachable chamber comprising a humidifying media for humidification of the sample environment confined within the chamber and separated from the sample so as to avoid potential damaging effects of humidity on the sample or on the device.

2. The device of claim 1, wherein the signal conditioning unit is a force sensing amplifier device.

3. The device of claim 1, wherein the frame further comprises a crossbar for receiving the load cell, said crossbar having a minimal mass and minimal vertical deflection for not increasing device compliance while still exerting minimal resting force on an attached load cell, to avoid damaging of the latter.

4. The device of claim 1, wherein the crossbar is slidably adapted onto the frame for sliding in a vertical direction, said crossbar being removably fixed at a given height on the frame by manual retention means.

5. The device of claim 4, wherein the retention means are butterfly bolts.

6. The device of claim 1, further comprising means for attaining fine vertical alignment with a sample fixed to the actuator.

7. The device of claim 6, wherein the means for attaining fine vertical alignment comprises an enlarged bore hole through the crossbar, two rigid washers on each side of the bore hole and a bolt traversing the hole attached to the load cell, whereby in use fine vertical alignment with the sample is achieved visually by sliding the bolt and washers across the crossbar using the tolerance provided by the enlarged bore diameter.

8. The device of claim 1, further comprising a test chamber for unconfined compression of a sample, said test chamber being mounted on the device for allowing the load cell to access within.

9. The device of claim 1, further comprising a test chamber for confined compression of a sample, said test chamber being mounted on the actuator and provided with a bore adapted in size to receive in a. fit-tight manner the load cell for measuring confined compression on a sample placed within said bore.

10. The device of claim 8, wherein the load cell is provided with an indentor for testing indentation of a sample.

11. The device of claim 1, further comprising a test chamber for tension testing of a sample attached therein, said load cell being provided with grips for retaining and pulling on one end of the sample.

12. The device of claim 2, further comprising a test chamber attached to and suspended from the load cell, said load cell being connected to the actuator supported by the crossbar, wherein the crossbar is mounted on the frame for vertical movement, said actuator, said load cell and said chamber being aligned in one axis.

13. The device of claim 1, further comprising a test chamber having a floor and being adapted for bending tests, said test chamber being provided with supports for supporting a sample above the floor of the chamber.

14. The device of claim 1, further comprising a test chamber provided with microelectrodes incorporated into said test chamber to detect electrical events caused by compression induced streaming potentials within the sample during testing.

15. The device of claim 1, further comprising a detachable chamber designed to be autoclave sterilized and to accept sterile specimens within an aseptic environment for testing in a sterile environment.

16. The device of claim 1, wherein an initial contact of the sample and the load cell is found using an automated computer controlled procedure where an algorithm applies a calculated displacement at a calculated velocity until a given value of contact force is detected by the cell load.

17. The device of claim 1, further comprising a programmable digitizing amplifier situated in the vicinity of the load sensing unit to i) minimize noise in the load signal by providing a digital signal representing the load with a precision of 1 part in 20,000 ii) accommodate interchangeable load cells with specific energizing and gain parameters, and iii) provide a second digital output indicating a user defined excess load (overload) condition on the load cell.

18. The device of claim 17, wherein the digital signal indicating excess load is directly coupled to the actuator controller to automatically execute a motor stop command in response to excess load.

19. The device of claim 1, wherein the actuator, provides a precision of 1–1000 nm with a range of at least 0.25–5 million times that value and executes a constant velocity motion, said actuator being controlled with a computer program to execute stress relaxation, ramp-release, dynamic sinusoidal and creep tests.

20. The device of claim 1, wherein, during a sinusoidal test, a sinusoidal displacement of the actuator is achieved using a computer algorithm concatenating a sequence of constant velocity steps to achieve an optimal precision and minimal distortion of the sinusoidal displacement, given the amplitude and frequency of the sinusoidal displacement, said algorithm finds a sequence of constant velocity steps which best approximate the sine wave given the performance characteristics of the actuator (including step size and velocity range).

21. The device of claim 1, wherein during a creep test a feedback control of the actuator is executed to maintain a constant sensed force on the load cell, a computer algorithm is used where an updated position is calculated to maintain a constant sensed force, based on the force and position history and performance characteristics of the actuator, step size and velocity range of the actuator.

22. The device of claim 1, wherein a signal conditioning and treatment include an interpolation algorithm to temporally align the position and force signals given known performance characteristics of a signal acquisition system including the delay time between acquisition of load and position.

* * * * *